US006337093B1

(12) United States Patent
Kim et al.

(10) Patent No.: US 6,337,093 B1
(45) Date of Patent: Jan. 8, 2002

(54) IMMUNOMODULATORY AND ANTIMICROBIAL MATERIALS, THEIR PREPARATION AND USE

(76) Inventors: Soo In Kim, 1-901, Hangang Apt., Jamwon-Dong, Seochio-ku, Seoul (KR); German Bekker, Germania Str. 62, D-45356 Essen (DE); Sergey I. Chernysh, Moscowski prospect, 171 app. 97, St. Petersburg (RU)

( * ) Notice: Subject to any disclaimer, the term of this patent is extended or adjusted under 35 U.S.C. 154(b) by 0 days.

(21) Appl. No.: 09/452,464

(22) Filed: Dec. 2, 1999

(30) Foreign Application Priority Data

Dec. 2, 1998 (EP) ............................................ 98122555

(51) Int. Cl.$^7$ .......................... A61K 35/64; A61K 35/12
(52) U.S. Cl. ....................................................... 424/538
(58) Field of Search ....................... 514/6, 21; 424/520, 424/538, 405

(56) References Cited

U.S. PATENT DOCUMENTS

| 4,355,104 A | * | 10/1982 | Hultmark et al. | 435/70 |
| 5,231,081 A | * | 7/1993 | Stiefel et al. | 514/6 |
| 6,063,765 A | * | 5/2000 | Bennich et al. | 514/12 |

FOREIGN PATENT DOCUMENTS

| EP | 299 828 | 1/1989 |
| EP | 320 528 | 6/1989 |
| EP | 856 519 | 8/1998 |
| WO | 81/03124 | 11/1981 |
| WO | 90/14098 | 11/1990 |

OTHER PUBLICATIONS

Levenbook et al. Calliphorin and Soluble Protein of Haemolymph and Tissues During Larval Growth and Adult Development of Calliphora Vicina; Insect Biochemistry, vol. 10 No. 6, pp. 693–701, 1980.*

U. Naumann et al., "Complete cDNA and Gene Sequence . . . and Arthropod Hemocyanins", Biochem. and Biophys. Res. Comm., vol. 177:3, 1991.

Chemicals Abstracts, vol. 124, No. 7, Feb. 1996, S. Chernysh et al., "The inducible anti bacterial peptides . . . insect defensing", p. 1111;XP002104565.

* cited by examiner

Primary Examiner—Christopher R. Tate
Assistant Examiner—Patricia D. Patten
(74) Attorney, Agent, or Firm—Heller Ehrman White & McAuliffe LLP

(57) ABSTRACT

The present invention is concerned with immunomodulatory and antimicrobial peptide materials obtainable from the body fluid of invertebrates, especially insects.

6 Claims, No Drawings

IMMUNOMODULATORY AND ANTIMICROBIAL MATERIALS, THEIR PREPARATION AND USE

The present invention is concerned with immunomodulatory and antimicrobial materials of invertebrate origin. In particular, the present invention is concerned with a composition, comprising a peptide or a peptide mixture of invertebrate origin and pharmaceutical preparations comprising such composition which are useful in the treatment of immune deficient conditions, infections and oncological diseases.

In the state of the art various pharmaceutical preparations of natural origin containing extractive materials of animal and plant tissues able to stimulate the immune system's efficacy as well as to kill pathogenic microorganisms directly are known.

A process for obtaining cellular protein having anti-HIV activity from CD4-positive T cells or myeloid cells is disclosed in U.S. Pat. No. 5,480,782.

A topic formulation comprising a Ginkgo biloba extract exhibiting antibacterial and antiviral properties is disclosed in DE 43 34 600 A1.

WO 96/04005 discloses a pharmaceutical composition for stimulation of the immune response of an organism comprising as the active ingredient major histocompatibility complex antigens extracted from animal tissues, serum or cells. The tissues, cells or sera are chosen from goat, veal or pig liver and bovine red blood cells.

A pharmaceutical composition containing an extract of the plant *Nigella sativa* is disclosed in U.S. Pat. No. 5,482,711 for treating cancer, preventing the side effects of anticancer chemotherapy, and for increasing the immune functions in humans.

It is known from scientific literature that insect tissues also contain antimicrobial proteins and peptides (Gillespie J. P., Kanost M. R. and Trenczek T. Biological mediators of insect immunity. Annu. Rev. Entomol., 1997, 42, 611–643; Hoffmann J. A. and Reichhart J-M. Drosophila immunity Trends in Cell Biology, 1997, 7, 309–316). These materials posses direct toxicity to bacteria and fungi.

The preparations mentioned above and analogous natural pharmaceutical preparations enhance the recent arsenal of medicines suitable for treatment of immune deficient conditions, infections and oncological diseases. However, the pharmaceuticals which are available up to now do not cover existing demands in immunomodulatory and antibiotic medicines.

Therefore, it is an object of the present invention to make available a pharmaceutical composition useful for treatment of immune deficient conditions, infections and oncological diseases.

It has been found that compositions comprising a peptide or a peptide mixture of invertebrate and in particular insect origin exhibit an immunomodulatory and antimicrobial activity. Therefore, the present invention is related to a composition, comprising a peptide or a peptide mixture, preparable by a process comprising the steps of collecting, centrifugating and chromatographically separating the body fluid of an invertebrate.

Moreover, the present invention is directed to pharmaceutical preparations, comprising the above composition.

The compositions of the present invention comprise a peptide or a peptide mixture. Herein, the term "peptide" refers to oligo- and polypeptides as well as to proteins. The peptides are believed to be the active principles in the pharmaceutical preparations prepared from these compositions. Nevertheless, the compositions may comprise further components which however should not interfere with the active principles in order to obtain useful pharmaceutical preparations.

The compositions of the present invention are preparable by a process comprising the steps of collecting, centrifugating and separating the body fluid of an invertebrate. The separation step can for example be carried out using a chromatographic column like a Sep-Pak C18 chromatographic column available from Waters Co., but other separation methods may also be used. If desired, further purification and concentration steps like lyophilisation may follow.

As source for the body fluid used for the isolation of the compositions of the present invention the following invertebrates have been found to be especially useful in the course of comparative investigations:

*Calliphora vicina, Musca domestica, Limnephilus stigma, Sialis lutaria, Isogenus nubecula, Palomena prasina, Podisus maculiventris, Pachyiulus flaviceps, Hemophisalis longicornis, Arenicola marina, Mitilus edulis, Mya arenaria, Asterias rubens, Stychopus japonicus, Halocynthia roretzi and Aurelia aurita.*

Preferably the hemolymph of an insect may be used as the body fluid of an invertebrate. The hemolymph of an insect *Calliphora vicina* Robineau-Desvoidy (*C. vicina*, Diptera, Calliphoridae) is especially preferred.

It should be understood that the compositions of the present invention may be obtained by extraction from the body fluid of a single invertebrate as well as from the body fluids of two or more different invertebrates.

Moreover, it has been found that the hemolymph of septically injured *C. vicina* larvae accumulates unusual high concentrations of antimicrobial materials as compared to other species investigated. This allows to use *C. vicina* hemolymph as raw material for the production of pharmaceutical preparations with combinative antibiotic and immunomodulatory activity.

The *C. vicina* larvae may for example be septically injured by pricking off cuticle with a needle soaked in a suspension of heat-killed *Escherichia coli* and *Micrococcus luteus* cells. It is of course also possible to use other pathogenic or nonpathogenic bacteriae like *Staphylococcus aureus* or different strains of Salmonella.

Another aspect of the present invention are pharmaceutical preparations comprising one or more of the above compositions.

These pharmaceutical preparations are useful as antibiotics. Due to their antibiotic activity the pharmaceutical preparations of the present invention directly kill pathogenic microorganisms thereby exhibiting antibacterial and/or antifungal activity.

In vitro studies showed that the pharmaceutical preparations of the present invention have strong antibiotic activity against a variety of Gram-positive and Gram-negative bacteria including important human pathogens. The pharmaceutical preparations are also found to be effective in vivo. Particularly, they are able to cure mice infected with a lethal dose of human pathogenic strains of *Klebsiella pneumonia* and *Salmonella typhimurium*. Their fungicidal activity includes both yeast like *Candida albicans* and *filamentous* fungi.

Moreover, the pharmaceutical preparations of the present invention possess an immunomodulatory activity on human and mammalian immune cells and are thus useful for the treatment or prevention of immune deficient conditions like oncological diseases, especially cancer, and viral infections.

The basic mode of the immunomodulatory action of the pharmaceutical preparations of the present invention is a stimulation of cytotoxic lymphocytes such as natural killer cells able to kill malignant or virus-infected cells. The pharmaceutical preparations for example enforce mouse spleen lymphocytes to attack cancer cells of various origin in vitro and in vivo. Furthermore, the preparations when injected to mice induce strong and prolonged synthesis of endogenous interferon, the principal cytokin activating various defense mechanisms of the immune system.

Extensive studies of the response of lymphocytes of human donor blood to the pharmaceutical preparations of the present invention confirm that the pharmaceutical preparations also have a strong immunomodulatory effect on a significant part of the human population.

It is known that mechanisms of natural cytotoxicity play an important role in the organism's protection against infection diseases as well as in the killing of the organism's own malignant cells (Trinchieri G. Biology of natural killer cells, Advances in Immunology, 1989, vol. 47, 187–375; Brittenden J., Heys S. D., Ross J. and Eremin O. Natural killer cells and cancer, Cancer, 1996, vol. 77, 1126–1243). Therefore, stimulators of the lymphocytes' natural cytotoxicity potentially may be used for the treatment and prevention of various infectious and cancer diseases caused by an insufficient efficacy of the cytotoxic mechanisms of innate immunity.

As for interferons, interleucins and other known immunomoludatory materials, the efficacy of the pharmaceutical preparations of the present invention is restricted by the basic capacity of the immune system to recognize and attack cancer cells. However, the efficacy may be enhanced when the pharmaceutical preparations are combined with other antitumor drugs. It has surprisingly been found that the pharmaceutical preparations of the present invention interact with different cytostatics and interferon and that some biocompatible combinations are active in cases when neither the known drug nor the pharmaceutical preparation is effective alone. Especially a combination of the pharmaceutical preparations of the present invention and bleomycin essentially suppressed tumor growth and increased life span even though each drug alone was much less effective. This synergistic effect between present pharmaceutical preparations and the known cytostatic bleomycin renders a combinative cancer immunochemotherapy possible which promises to be a most effective way to cancer treatment.

Instead of the compositions obtained from the body fluid of invertebrates the isolated or synthesized active principles of these compositions may be used for the preparation of the pharmaceutical preparations of the present invention. An active immunomodulatory principle of the composition of the present invention has been isolated. Preliminary data on the principle's activity show that it is able to stimulate the cytotoxic anticancer activity of human and mouse lymphocytes in vitro as well as to induce in mice the lymphocytes' cytotoxicity and the interferon production in vivo. A unique peculiarity of the active principle's mode of action is its ability to stimulate the activity of the lymphocytes at extreme low concentrations. The minimum effective concentration was determined to be about 0.0005 nanogram/ml. The optimum concentration was found to be 0.05–0.5 nanogram/ml. In that case it stimulates the cytotoxicity of lymphocytes more effectively than interferon, a specific human cytokin responsible for the activation of lymphocytes.

A comparative analysis of the minimum active concentrations of an active principle of a composition of the present invention and the known human regulatory peptides interleucin, interferon, tumor necrosis factor, defensin and NK-lysin shows a clear advantage of the active principle. It works at an essentially less concentration as compared to any human cytokin including interleucin, the most active immunomodulator known so far. For the human cytolitic peptides NK-lysin and defensin which directly kill the target cells their concentration to enhance cancer cell destruction even exceeds the effective concentration of the active principle more than a million times.

Moreover, the compositions of the present invention and their active principles are effective stimulants of cytotoxic lymphocytes like NK-cells and cytotoxic T-cell and demonstrate potent antiviral activity when tested using as a model mice infected by human influenza virus A or B. In this model wild type males were infected intranasally by a suspension of the human influenza virus A or B and the pharmaceutical preparations were injected intraperitoneally one day before infection and then 1, 2, 4, 6 and 8 days after. Both, a composition of the present invention and its active principle effectively protected mice from pulmonary lesions and death. Thus, the composition and its active principle are useful in the preparation of a pharmaceutical preparation for the treatment or prevention of viral infections.

Neither an acute nor a chronic toxicity of the composition of the present invention or its active principle was found in the course of in vivo and in vitro studies.

It is understood that the pharmaceutical preparations of the present invention may also comprise conventional additives like excipients or carriers. The preparations may be administered to the patient by enteral, such as oral or rectal, and parenteral, such as intraperitoneal, intramuscular, intravenous or subcutaneous route. The preparations may be administered in dosage forms such as capsules, tablets and suppositories. For parenteral use the pharmaceutically active components are preferably in the form of an injectable solution.

The invention is further illustrated by the following examples:

EXAMPLE 1

Manufacturing of the Preparation from *C. vicina*

Postfeeding *C. vicina* larvae maintained in the laboratory conditions as described (Chernysh S. I., Simonenko N. P., Numata H. Sensitive stage for the diapause averting effect of high temperature in the blowfly, *Calliphora vicina* (Diptera, Calliphoridae) Appl. Entomol. Zool., 1995, Vol. 30, No. 3, p. 498–499) were bacteria challenged by pricking off cuticle with a needle soaked in a suspension of heat-killed *Escherichia coli* and *Micrococcus luteus* cells. The hemolymph of septically injured larvae was collected, centrifuged and applied onto a Sep-Pak C18 chromatographic column (Waters Co). The column was washed with 0.05% trifluoroacetic acid. Then the target materials were eluted with 50% acetonitril acidified with 0.05% trifluoroacetic acid. The eluted fraction was lyophilized and used as the preparation. The preparation output was equal to 3.3% of hemolymph dry matter.

EXAMPLE 2

Antimicrobial Activity of the Preparation 2.1 Methods of Analysis

The antimicrobial activity was measured by means of a standard plate growth inhibition assay and a liquid growth inhibition assay.

Plate Growth Inhibition Assay

Sterile Petri dishes (9 cm diam.) received 7.5 ml of melted agarose in Luria-Bertany (LB) medium (Difco) diluted 5 times to compare with the standard protocol (bactotrypton 1%, yeast extract 0,5%, NaCl 1%). $2 \times 10^5$ cells of the given bacterial strain per one Petri dish were added in the warm medium before its solidification. 2 microliter samples of material were placed on the medium surface. The plates were incubated 24 h at 37° C. and the size of the inhibition zone of the bacterial growth was measured.

Liquid Growth Inhibition Assay

A sterile liquid LB medium was inoculated with log-phase bacterial cells ($10^4$ cells/ml) and placed in wells of microtitration plates as 95 microliter aliquots. 5 microliter aliquots of tested material were placed in each well. Equal volumes of sterile water were added in control wells. The plates were incubated 24 h at 37° C. Then the vials were visually screened under the microscope and with an ELISA microplate reader. Then 5 microliter aliquots were taken from each well, placed on the surface of a sterile agar medium as a series of touches and incubated again at 37° C. from 1 to 5 days depending of the species of bacteria. The number of colony forming units (CFU) was counted according to the standard bacteriological protocol.

2.2 Comparative Activity of C. Vicina Preparation and Analogous Preparations Obtained from Other Animal Species In the course of a broad screening, the C. vicina preparation of Example 1 was compared with analogous preparations manufactured by the same method as mentioned in Example 1 from representatives of 8 classes and 18 families of invertebrates.

A solid growth inhibition assay was performed against two bacteria: Escherichia coli D31 (Gram negative bacteria) and Micrococcus luteus (Gram positive bacteria). The results are shown in Table 1 which comprises the maximum antibacterial activity in the hemolymph and analogous tissues of various invertebrates as compared to the antibacterial activity in C. vicina hemolymph. As one can see from Table 1, the preparations obtained from invertebrates exhibit an antibacterial activity whereby however none of the species investigated possesses more then 10% of antibacterial activity as compared to the C. vicina preparation.

In Table 1 comparative data on the antibacterial activity in the hemolymph of normal, nonimmunized larvae is also shown. As one can see, bacterial challenge dramatically increases the antibacterial activity of the hemolymph and makes C. vicina the most rich source of antimicrobial materials as compared to both nonimmunized insects of the same species and immunized animals of other species.

TABLE 1

| Species | Taxon | Antibacterial activity per ml tissue in % to C. vicina | |
|---|---|---|---|
| | | E. coli | M. luteus |
| INSECTA | | | |
| Calliphora vicina (immune larvae) | Diptera | 100 | 100 |
| Calliphora vicina (normal larvae) | Diptera | <1 | <10 |
| Musca domestica | Diptera | <10 | <10 |
| Limnephilus stigma | Trichoptera | <10 | <10 |
| Sialis lutaria | Megaloptera | 0 | <10 |
| Isogenus nubecula | Plecoptera | <1 | <1 |

TABLE 1-continued

| Species | Taxon | Antibacterial activity per ml tissue in % to C. vicina | |
|---|---|---|---|
| | | E. coli | M. luteus |
| Palomena prasina | Hemiptera | <10 | <10 |
| Podisus maculiventris | Hemiptera | <10 | <10 |
| OTHER ARTHROPODA | | | |
| Pachyiulus flaviceps | Diplopoda | <10 | <10 |
| Hemophisalis longicornis | Acarina | 0 | <1 |
| OTHER INVERTEBRATES | | | |
| Arenicola marina | Polychaeta | <1 | 0 |
| Mitilus edulis | Mollusca | <1 | <1 |
| Mya arenaria | Mollusca | 0 | <10 |
| Asterias rubens | Echinodermata | <10 | <10 |
| Stychopus japonicus | Echinodermata | <1 | 0 |
| Halocynthia roretzi | Tunicata | <10 | <10 |
| Aurelia aurita | Coelenterata | 0 | <10 |

2.3 Qualitative and Quantitative Analysis of Antimicrobial Activity of the Preparation Data on the antimicrobial activity of the preparation of Example 1 obtained by the liquid growth inhibition assay are summarized in Table 2. High sensitivity to the preparation was found in all strains of E. coli, K. pneumonia and C. albicans, intermediate sensitivity was found in B. thuringiensis. Sensitivity of these strains and also M. luteus was confirmed by a solid growth inhibition assay as well. Only Sthaphylococcus aureus was found to be relatively resistant to the preparation.

TABLE 2

| Strain | Taxon | MIC*, microgram/ml | Mode of action** |
|---|---|---|---|
| Escherichia coli 0144 | Enterobacteria | 11 | bactericidal |
| Klebsiella pneumonia | Enterobacteria | 11 | bactericidal |
| Candida albicans | Ascomycetes | 11 | fungicidal |
| Bacillus thuringiensis (var. Kenya) | Bacillaceae | 110 | bactericidal |
| Staphylococcus aureus | Coccaceae | 2000 | bacteriostatic |

*MIC-minimum inhibitory concentration
**the mode of action was determined by transfer of microbial cells incubated one day in the presence of the preparation onto fresh agar medium and subsequent count of the number of colony forming units

EXAMPLE 3

Immunomodulatory Activity of the Preparation

The determination of the immunomodulatory activity of the preparation of Example 1 comprises the stimulation of the human peripheral blood lymphocytes' and the mouse spleen lymphocytes' ability to kill cultivated cancer cells in vitro. In most experiments the K562 human leukemia cell line's specific sensitivity to natural killer cells was used as a target for the measurement of the lymphocytes' cytotoxic activity. Moreover, a mouse hepatoma cell line was used as an additional model.

3.1 The Preparation's Effect on Mouse Spleenocytes' Cytotoxicity in Vitro

To analyze the effect of the preparation of Example 1 on the mouse spleen lymphocytes' cytotoxic activity, the standard cytotoxicity assay was used (Hasimoto J. and Sudo E. Evaluation of cell damage in immune reaction by release of radioactivity from H3-uridine labelled cells, Gann, 1971, vol. 62, 139–145; Filatova N. A., Malygin A. M., Goryunova L. B., Fel V. Ya. and Khavinson V. K. Immunomodulation of natural killer activity of C3HA mice splenocytes during hepatoma 22a growth., Tsitologia, 1990, Vol. 32, No. 6, 652–658). H3-uridine labeled mouse hepatoma cells and K562 cells were used as targets for a cytotoxic lymphocytes' attack. Fresh spleen lymphocytes and target cells were co-incubated during 18 hours in the presence or absence of the preparation. Then the proportion of killed and normal target cells and the corresponding cytotoxicity index were determined in control and experimental groups. Data on the preparation's effect on the lymphocytes' cytotoxicity of mouse spleen against the H3-uridine labeled K562 cell line are summarized in Tables 3 and 4. Each figure in the Tables summarizes results of 24 independent cytotoxicity determinations. A statistically significant increase in the cytotoxicity index was found both in mice with low (Table 3) and high (Table 4) initial spleen lymphocytes' activity even though the conventional efficacy of the preparation was higher when the initial level of lymphocytes' activity was lower. The minimum effective concentration was determined as less then 5 nanograms per ml. The stimulatory effect of the preparation on the cytotoxic activity of the spleen lymphocytes was also found when mouse hepatoma cells were used as targets (data not shown).

TABLE 3

| Concentration, | Cytotoxicity index | |
|---|---|---|
| nanogram/ml | % | % to control |
| 0 | 22.7 ± 3.0 | 100 |
| 500 | 43.2 ± 4.5*** | 190 |
| 5000 | 36.9 ± 4.6** | 163 |
| 50000 | 34.7 ± 4.7* | 153 |

*$P < 0.05$; $P < 0.01$; *$P < 0.001$

TABLE 4

| Concentration, | Cytotoxicity index | |
|---|---|---|
| nanograms/ml | % | % to control |
| 0 (control) | 58.3 ± 2.4 | 100 |
| 5 | 73.3 ± 3.7*** | 126 |
| 50 | 68.5 ± 3.9* | 117 |
| 500 | 69.7 ± 3.9** | 120 |
| 5000 | 69.3 ± 3.7** | 119 |
| 50000 | 67.1 ± 3.9– | 115 |

–$P > 0.05$; *$P < 0.05$; $P < 0.01$; *$P < 0.001$ 3.2 The Preparation's Effect on the Mouse Spleen Lymphocytes' Cytotoxic Activity in Vivo The in vivo immunomodulatory effect of the preparation when injected into mouse in appropriate doses is described. Mice of the C3HA genotype were injected intraperitoneally in a single dose 5 to 500 microgram (0.25–25 mg/kg) of the preparation dissolved in 0.1 ml of saline. Control mice were injected with 0.1 ml of saline also. 4 mice in each experimental group were used. 24 hours later spleen was rejected, lymphocytes were released from the spleen and their cytotoxicity was evaluated against K562 target cells as mentioned above. The data in Table 5 summarize the results of 70 individual measurements under a lymphocyte:target ratio of 5:1 and 20:1. These data show that the injection of 50 microgram of the preparation provoked a significant increase in the lymphocytes' cytotoxicity against target cancer cells.

Therefore, we conclude that the preparation is active as stimulant of lymphocytes' cytotoxicity in vivo as well as it was shown above in vitro.

TABLE 5

| | Cytotoxicity index under lymphocyte: K562 cells ratio | | | |
|---|---|---|---|---|
| Dosage | 5:1 | | 20:1 | |
| microgram per mouse | % | % to control | % | % to control |
| 0 (control) | 11.9 ± 4.1 | 100 | 20.9 ± 1.9 | 100 |
| 5 | 13.0 ± 1.9– | 109 | 26.5 ± 1.6** | 127 |
| 50 | 30.1 ± 3.3*** | 253 | 37.4 ± 2.6*** | 179 |
| 500 | 18.0 ± 2.8– | 151 | 22.7 ± 2.3– | 109 |

–$P > 0.05$; *$P < 0.05$; $P < 0.01$; *$P < 0.001$ 3.3 The preparation's Effect on the Cytotoxicity of Human Lymphocytes in Vitro An example of the preparation's effect on the cytotoxic activity of human peripheral blood lymphocytes (PBLs) against cultivated K562 cells is shown in Table 6. Lymphocytes were released from fresh donor blood and purified of erythrocytes by centrifugation using the histopak 1077 solution (Sigma). After centrifugation the lymphocytes were resuspended in phosphate buffer, centrifuged and resuspended again in RPMI 1640 medium supplemented with glutamine, gentamycin and RNAase. The lymphocytes were diluted up to $2 \times 10^6$ cells/ml and immediately used for the cytotoxicity analysis as mentioned above. Each figure in Table 6 summarizes the results of 10 cytotoxicity measurements.

The PBLs cytotoxicity against K562 cancer cells was significantly increased when the preparation was added to the incubation medium in a concentration starting from 0.005 nanogram/ml, however, the stimulatory activity reached a plato at a concentration of about 5 nanogram/ml.

Further studies demonstrate that the donor's sensitivity to the presence of the preparation varies depending on the basal PBLs cytotoxic activity. The most evidential stimulatory activity was found in donors with a low PBLs cytotoxic activity against K562 cells when the cytotoxicity index in the control was less then 30%. No clear stimulatory activity was found in donors with a very high basal PBLs activity (cytotoxicity index in the control is more then 50%). Therefore, we suppose that the preparation might be used for treatment of patients suffering of depressed cytotoxic lymphocytes activity.

TABLE 6

| Concentration, nanogram/ml | Cytotoxicity index % |
|---|---|
| 0 (control) | 25.2 ± 3.1 |
| 0.0005 | 30.4 ± 1.3– |
| 0.005 | 38.5 ± 2.1** |
| 0.05 | 37.8 ± 1.9** |
| 0.5 | 43.8 ± 2.7*** |
| 5 | 51.1 ± 2.02*** |
| 50 | 49.0 ± 2.2*** |
| 500 | 54.7 ± 2.1*** |

–$P > 0.05$; $P < 0.01$; *$P < 0.001$

EXAMPLE 4

Antitumor Activity of the Preparation

The antitumor activity of the preparation of Example 1 was checked on mice and rats challenged by various cancer cells. The therapeutic effect was different depending on origin and specific properties of the cancer cells. No positive response was found on wild type mice challenged with Erlich ascite cancer cells and on mice of C5781 genotype challenged with melanoma B16 cancer cells. A weak anti-cancer activity was found in mice of DBA genotype intravenously challenged by leukemia P388 cells (increase in life span) and in rats intravenously challenged by rabdomyosarcoma cells (decrease in average size of lung metastases).

However, a significant solid tumor suppressive activity was found in mice of C3HA genotype challenged by syngenic mouse hepatocarcinoma 22a cells during 17 days postinoculation (Table 7). The mice were challenged subcutaneously by $3 \times 10^5$ hepatocarcinoma cells. The preparation was injected subcutaneously one day later and same injections were repeated once a week. Each experimental group included 10 animals. A clear dose dependent suppression of tumor growth was established in animals receiving the preparation. In the group provided with 500 micrograms of the preparation, only 30% of the mice had visible subcutaneous tumors during 17 days postinoculation as compared to 90% in the control (saline injected) group. Even if tumors appeared, their average size was significantly decreased as compared to the control animals.

These data confirm the anticancer activity of the preparation in certain tumors presumably sensitive to immunological surveillance as we can suppose from our recent knowledge of the immunomodulatory activity of the preparation.

TABLE 7

| Injected dose, microgram/mouse | % of tumor bearing animals | Average tumor linear size mm | % to control |
|---|---|---|---|
| 0 (control) | 90 | 22.3 ± 3.4 | 100 |
| 5 | 80 | 13.5 ± 2.5* | 61 |
| 50 | 80 | 14.7 ± 3.4 | 66 |
| 500 | 30** | 2.6 ± 1.4*** | 12 |

*P < 0.05; P < 0.01; *P < 0.001

EXAMPLE 5

Antiviral Activity in Animal Models

To determine the antiviral activity of the preparation of Example 1, wild type mouse males were intranasally infected with strains of human influenza virus A or B virulent to mice. The preparation was injected intraperitoneally one day before infection then 1, 2, 4, 6 and 8 days after. The mortality of the infected mice 10 days after virus inoculation is given in Tables 8 (virus A) and 9 (virus B).

The preparation effectively protected mice of pulmonary lesions death caused by both virus infections. It is important to that influenza virus B has no effective chemotherapy so far.

TABLE 8

| Treatment | Dosage, microgram per mouse | N | Mortality 10 days after virus inoculation, % |
|---|---|---|---|
| Control | — | 20 | 70 |
| Preparation | 250 | 15 | 33 |

TABLE 9

| Treatment | Dose, µg/mouse | N | Mortality 10 days after virus inoculation, % |
|---|---|---|---|
| Control | — | 11 | 80 |
| Preparation | 250 | 10 | 36 |

EXAMPLE 6

Toxicity of the Preparation

To evaluate the acute toxicity, the preparation of Example 1 in the dose from 0.6 to 5.0 mg was injected intraperitoneally in 0.25 ml saline (0.9% NaCl) to wild type male mice having 18–20 g weight. Each of 4 experimental groups included 3 animals. After 48 hours exposition, the animals were euthanized and dissected. No one animal had signs of pathological response. The mice were active and did not loose weight. Inner organs (liver, spleen, adrenal glands, gall-bladder, mucous membranes) were without visible alterations. Thus, the preparation seems to have no acute toxicity when injected in a single dose up to 5 mg per animal (about 100 mg/kg) which exceeds the proposed therapeutic dose up to 100 times.

The preparation was also applied intravenously as a 1 mg single dose to 10 mice without any signs of acute toxicity.

Furthermore, the preparation's toxicity was tested in vitro using cultivated K562 human cells and fresh human erythrocytes.

The K562 cells were incubated in the RPMI 1640 cell culture medium in the presence of various concentrations of the preparation (Table 10). After 1 or 2 days of incubation the cells were stained by tripan blue and the number of normal (unstained) and damaged (stained) cells was counted. The data in Table 10 summarizes the results of 10 independent experiments. The number of damaged cells in the population was not significantly increased even if the preparation's concentration in the medium was 500 microgram/ml. Assuming that the preparation's minimum effective immunomodulatory concentration in vitro is less then 1 nanogram/ml (see Example 3), we conclude that the preparation has no toxicity to K562 cells in vitro.

These data also confirm that the increase of the lymphocytes' cytotoxicity as well as the tumor suppressive activity demonstrated above in Examples 3 and 4 can not be attributed to the preparation's direct cytotoxicity.

TABLE 10

| Concentration, micrograms/ml | % of damaged stained cells in the population | |
|---|---|---|
| | 1 day incubation | 2 day incubation |
| 0 (control) | 4.9 ± 1.1 | 3.7 ± 0.4 |
| 0.5 | 4.4 ± 0.6 | 1.5 ± 0.2 |
| 5 | 6.3 ± 1.2 | 3.7 ± 0.4 |
| 50 | 4.8 ± 0.6 | 4.2 ± 0.4 |
| 500 | 6.0 ± 1.0 | |

The preparation's hemolytic activity was tested on fresh erythrocytes released from the donor blood of 4 antigenic groups (Table 11). No signs of hemolysis were found in a concentration range of the preparation up to 400 microgram/ml. A limited hemolysis was visible at a concentration of 800 microgram/ml among erythrocytes of II and III but not I and IV antigenic groups. The last concentration exceeds the minimum immunomodulatory concentration about 1 million times.

Thus, summarizing the available results of the in vivo and in vitro toxicity evaluations, we conclude that the preparation has no toxicity in concentrations dramatically exceeding the supposed therapeutic doses.

TABLE 11

| Blood antigenic group | The preparation concentration, micrograin/ml |      |    |    |     |     |     |     |
|---|---|---|---|---|---|---|---|---|
|   | 0 | 6.25 | 12.5 | 25 | 50 | 100 | 200 | 400 | 800 |
| I   | − | − | − | − | − | − | − | − | −  |
| II  | − | − | − | − | − | − | − | − | ++ |
| III | − | − | − | − | − | − | − | − | +  |
| IV  | − | − | − | − | − | − | − | − | −  |

Hemolysis rate:
− no
+ trace
++ limited
+++ intensive
++++ full

What is claimed is:

1. An antimicrobial/anti-tumor composition, comprising a peptide or a peptide mixture, obtained by a process comprising the steps of:

(a) vaccinating an invertebrate with a bacterium; and (b) collecting, centrifuging and chromatographically separating the body fluid of said invertebrate to obtain a fraction containing said antimicrobial/anti-tumor composition, wherein said invertebrate is *Calliphora vicina*.

2. The composition of claim 1, wherein the body fluid is the hemolymph.

3. The composition of claim 2, wherein the invertebrate is a septically injured *Calliphora vicina* larva.

4. A composition, comprising said composition of claim 2, and a pharmaceutically acceptable excipient.

5. A process for preparing a composition according to claim 1, comprising the steps of (A) collecting, centrifuging and chromatographically separating the body fluid of an invertebrate and (B) concentrating components of the body fluid obtained from step (A), wherein said invertebrate is *Calliphora vicina*.

6. A method for the treatment of the influenza virus, comprising administering to a patient in need thereof a composition that comprises a peptide or a peptide mixture, wherein said peptide or peptide mixture is obtainable by a process comprising the steps of collecting, centrifuging and chromatographically separating the body fluid from an invertebrate, wherein said invertebrate is *Calliphora vicina*.

* * * * *

UNITED STATES PATENT AND TRADEMARK OFFICE
CERTIFICATE OF CORRECTION

PATENT NO. : 6,337,093 B1
DATED : January 8, 2002
INVENTOR(S) : Soo In Kim, German Bekker and Sergey I. Chernysh It is certified that error appears in the above-identified patent and that said Letters Patent is hereby corrected as shown below:

<u>Title page,</u>
Item [75] - Inventor, delete "Seochio-ku" and replace with -- Seocho-ku --; and delete "Moscowski" and replace with -- Moscowskij --.

Signed and Sealed this

Fourth Day of June, 2002

*Attest:*

*Attesting Officer*

JAMES E. ROGAN
*Director of the United States Patent and Trademark Office*